United States Patent [19]

Kuwana et al.

[11] Patent Number: 5,426,193

[45] Date of Patent: Jun. 20, 1995

[54] PURIFIED 3,4-EPOXYCYCLOHEXYL (METHYL)ACRYLATE, A PROCESS FOR THE PREPARATION THEREOF AND A 3,4-EPOXYCYCLOHEXYL METHYL (METH)ACRYLATE COMPOSITION

[75] Inventors: Akihiro Kuwana, Otake; Kimihide Honda; Kunio Koga, both of Himeji, all of Japan

[73] Assignee: Daicel Chemical Industries, Inc., Saka, Japan

[21] Appl. No.: 301,234

[22] Filed: Sep. 6, 1994

Related U.S. Application Data

[60] Division of Ser. No. 109,320, Aug. 19, 1993, which is a continuation-in-part of Ser. No. 866,134, Apr. 9, 1992, abandoned.

[30] Foreign Application Priority Data

Aug. 28, 1991 [JP] Japan .................................. 3-216798
Dec. 5, 1991 [JP] Japan .................................. 3-321724

[51] Int. Cl.$^6$ .................. C07D 301/30; C07D 303/16
[52] U.S. Cl. ..................................... 549/202; 549/546
[58] Field of Search ........................ 549/202, 546

[56] References Cited

U.S. PATENT DOCUMENTS

| | | | |
|---|---|---|---|
| 3,001,975 | 9/1961 | Beavers et al. ................... | 549/202 |
| 3,040,076 | 6/1962 | Seidel et al. ......................... | 549/202 |
| 4,755,262 | 7/1988 | Matsunaga et al. ............... | 549/202 |

*Primary Examiner*—Joseph E. Evans

[57] ABSTRACT

Disclosed are the improvements of a process for the preparation of a purified 3,4-epoxycyclohexyl methyl (meth)acrylate and 3,4-epoxycyclohexyl methyl (meth)acrylate which is prepared by the improvements, including only minor amounts of polymers having a low molecular weight composed of 3,4-epoxycyclohexyl methyl (meth)acrylate itself.

Furthermore, disclosed is a 3,4-epoxycyclohexyl methyl (meth)acrylate composition which has an excellent resistance to coloring, including a specified organic phosphorous compound.

1 Claim, No Drawings

PURIFIED 3,4-EPOXYCYCLOHEXYL (METHYL)ACRYLATE, A PROCESS FOR THE PREPARATION THEREOF AND A 3,4-EPOXYCYCLOHEXYL METHYL (METH)ACRYLATE COMPOSITION

This is a divisional of application Ser. No. 08/109,320 filed Aug. 19, 1993, now allowed, which in turn is a continuation-in-part of Ser. No. 07/866,134, filed Apr. 9, 1992 now abandoned.

FIELD OF THE INVENTION

The present invention relates to a purified 3,4-epoxycyclohexyl methyl (meth)acrylate, a process for the preparation thereof, and a 3,4-epoxycyclohexyl methyl (meth)acrylate composition.

In particular, the present invention relates to the improvements of a process for the preparation of a purified 3,4-epoxycyclohexyl methyl (meth)acrylate.

BACKGROUND OF THE INVENTION

Heretofore, there has been widely known various acrylate monomers such as methylacrylate, ethylacrylate, 2-ethylhexyl acrylate, etc., which are monofunctional monomers, and trimethylolpropane triacrylate, pentaerythritol triacrylate, etc., which are multifunctional monomers.

However, the monofunctional monomers have a disadvantage that an odor of the residual monomer after curing causes a remarkable problem in the case of using as a component of printing inks or coatings.

Furthermore, the multifunctional monomers also have a disadvantage that it is necessary to be used in large amounts to resins in the case of using as a diluent of printing inks or coatings, resulting in loss of excellent properties of the resins.

On the other hand, cyclohexyl methyl (meth)acrylate itself is readily polymerized or copolymerized with other compounds having unsaturated groups by heat, ultraviolet rays and or ionized radiations at the presence of an initiator for the radical polymerization.

In particular, an epoxidized cyclohexyl methyl (meth)acrylate which an alicyclic epoxy group capable of being cured by a cation, that is, 3,4epoxycyclohexyl methyl (meth)acrylate is useful for polymerizing or copolymerizing.

3,4-epoxycyclohexyl methyl (meth)acrylate is low in viscosity and mild in odor, and has the solubility to resins over a wide range, and further it is useful for inks, coatings, adhesives, covering agents and a raw material for molding resins or a modifier thereof.

It is noted that there have been basically known 3,4-epoxycyclohexyl methyl (meth)acrylate and a process for the preparation thereof, specifically by the esterification reaction of tetrahydrobenzyl alcohol with (meth-)acrylic acid or by the transesterification reaction of tetrahydrobenzyl alcohol with a (meth)acrylate ester and successively by the epoxidation reaction with a peracid [Batog, A. E.; Zaitsev, S. Yu.; Kiryushima, N. P.; Zaitseva, V. V. (Inst. Fiz.-Org. Khim. Uglechim., Donetsk, USSR). Zh. Ors. Khim, 1982, 18(1), 90-4 (Russ)].

The reaction schemes are represented by the following formulae;

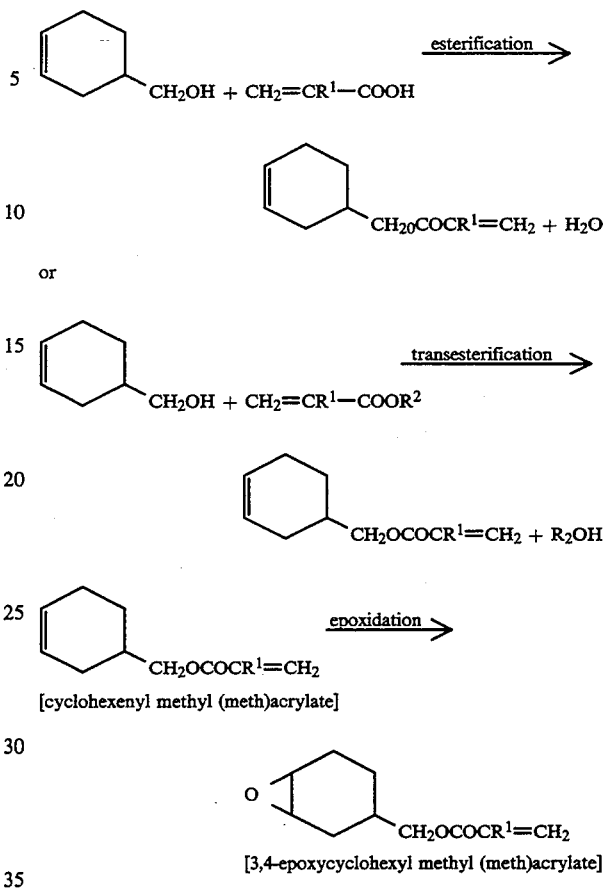

[in the formulae, $R^1$ is hydrogen or a methyl group, $R^2$ is an alkyl group].

However, a process for the preparation of a purified, that is, a commercially available 3,4-epoxycyclohexyl methyl (meth)acrylate, has not been disclosed up to date.

In particular, there has not been known such a process that even a waste water treatment is taken into consideration or even a small amount of impurity detected by a heptane test described hereinafter can be removed.

On the other hand, it has been known that 3,4-epoxycyclohexyl methyl (meth)acrylate has a disadvantage of exceedingly readily polymerizing, particularly, through the preparation processes, while being stored and or shipped under the influence of heat, lights or other causes.

In order to solve the disadvantage, Japanese Patent Unexamined Publication (Kokai) No. 282,574/1990 teaches a method for preventing polymerization, which uses quinones, etc. together with phosphorous compounds under the presence of molecular state oxygen gas.

However, it has been found by the present inventors that the effect by the method described hereinabove in which the polymerization inhibitors are used is not sufficient in the case of preparation processes on a commercial basis.

It is one of reasons why the effect by the method was not sufficient that there was not able to anticipate sufficient qualities to be possessed in a product of 3,4-epoxycyclohexyl methyl (meth)acrylate, which was not produced on a commercial basis in those days when the Publication was filed.

Specifically describing, it requires that low boiling components in a commercially available 3,4-epoxycyclohexyl methyl (meth)acrylate must be removed to the extent of from 2 to 3%, more preferably, not more than 1%.

For that purpose, it requires that heating temperatures are raised and or that processing time of period is extended in the step of removing the low-boiling ingredients.

However, raising up of the temperatures or extension of processing time of period generates, even though minor amounts, the polymers in a product.

It has been found that the polymers in a product cause problems even though such minor amounts through the advanced developments in relation to a commercially available 3,4-epoxycyclohexyl methyl (meth)acrylate.

For example, it is one of the problems that the polymers ooze out as adhesive and insoluble substances in the case of preparing intermediate materials of resins for coatings using 3,4-epoxycyclohexyl methyl (meth)acrylate including the polymers, resulting in causing various problems through processing and in producing coatings having a remarkably spoiled commercial valuation.

It appears that the minor amounts of polymers in a commercially available 3,4-epoxycyclohexyl methyl (meth)acrylate are composed of the polymers of 3,4-epoxycyclohexyl methyl (meth)acrylate itself having a low molecular weight.

The contents of such polymers having a low molecular weight can be shown by weight % with a measuring method using n-heptane or n-hexane, in which 10 g of a product is dissolved in 100 cc of n-heptane or n-hexane and resulting suspensions are filtered and weighed (hereinafter, occasionally referred to as HT or HT value in a solubility test).

It is known that a commercially available 3,4-epoxycyclohexyl methyl (meth)acrylate must exhibit the HT value of not more than 0.1% by weight.

It was found that the method described in Japanese Patent Unexamined Publication (Kokai) No. 262594/1990 only can provide 3,4-epoxycyclohexyl methyl (meth)acrylate having the polymer contents of more than 0.1% by weight in HT value, more specifically, 0.14% by weight or so, which values are not sufficient in quality, by a recollected confirmation test using HT carried out thereafter.

That is, further more effective methods for inhibiting polymerizing in each step of the preparation processes must be developed in order to produce a purified 3,4-epoxycyclohexyl methyl (meth)acrylate on a commercial basis.

It is noted that 3,4-epoxycyclohexyl methyl (meth)acrylate has an alicyclic epoxy group which tends to exceedingly readily react with an organic acid derived from an organic peracid which is an epoxidation agent, for example, the epoxy group reacts with acetic acid derived from peracetic acid in the case of using peracetic acid as an organic peracid, resulting in polymerization of 3,4-epoxycyclohexyl methyl (meth)acrylate and opening of the epoxy group, particularly through an evaporation step.

Accordingly, it is required that the organic acid is removed from a crude reaction solution as early as possible in order to maintain a short time of period contacting with the epoxy group.

Such more effective methods do not have been developed up to date.

Furthermore, it is noted that, heretofore, various processes for removing the organic acid and organic peracid:

(a) a refining process by distillation;

In the case of a heat resistible product, this process has been usually carried out.

(b) a refining process by extraction with water;

The organic acid or organic peracid, which are dissolved in a crude reaction solution, is primarily removed by an extraction with water and successively by distillation, in order to prevent the polymerization or the side reaction of an epoxy compound on distilling the crude reaction solution without any refining processes.

(c) a refining process by neutralization; have been applied.

In the case of incapability of removing the organic acid or organic peracid or in the case that the organic acid in an aqueous solution readily reacts with an epoxy compound, this neutralization process has been usually applied.

Furthermore, in the case of incapability of removing the substances in which the polymerization and the side reaction are caused, by merely adjusting to neutralization point of PH of the solution, the substances are occasionally removed with an aqueous alkali solution.

Distillation is carried out in order to refine after removing the substances by neutralization.

However, the prior art (a) is often incapable of being applied, because it has a disadvantage that there are caused the polymerization or the opening reaction of epoxy groups by distillation alone because of easiness in the reaction of epoxy groups with an organic acid.

Furthermore, the prior arts (b) and (c), which are often applied in the case of incapability of applying the prior art (a), are also often incapable of being applied in the case of the rapid reaction velocity of epoxy groups with an organic acid.

Still further, the prior art (c) is often incapable of putting into practice on an industrial basis because of not only large amounts of a product loss but also a considerable load in water treatments.

As mentioned above, the prior arts (a), (b) and (c) include difficult disadvantages, respectively, in the case of applying on an industrial basis.

That is, the prior arts (a), (b) and (c) have been industrially incapable of being applied to an epoxy compound having properties that a crude reaction solution can not be refined by distillation alone because of the polymerization, the side reaction and that an epoxy group tends to rapidly react with an organic acid and or water.

A first aspect of the present invention relates to a method for reducing a contacting time of period between an organic solution layer and an aqueous solution layer on extracting an organic acid and an organic peracid with water from a crude reaction solution after the epoxidation reaction.

The first aspect has been found based on the mechanism in which the loss of an epoxidized product is caused by the reaction of the epoxidized product dissolved into water solution with water and an organic acid and a resultant concentration reduction of the epoxidized product and further repeatedly resultant dissolving, that is, by the form of a reaction-extraction which accelerates further dissolving into water.

A centrifugal extractor is essentially used and retention time of period therethrough is essentially adjusted within 5 minutes in the first aspect, whereby the reaction of an epoxy compound with an organic acid and water is not caused so much.

A second aspect of the present invention relates to a method for further removing small amounts of them by extracting an organic acid and organic peracid with water, and more specifically the method comprises neutralization with an alkali after separating with the apparatus as mentioned above.

It is noted that even though the centrifugal extractor as mentioned above is used in order to remove almost of the organic acid and organic peracid by extracting with water, there can not be removed small amounts of them.

And, there is a disadvantage in a product of 3,4-epoxycyclohexyl methyl (meth)acrylate refined by distillation in order to remove solvents and other low boiling components such as small amounts of starting materials after removing the organic peracid by extracting alone with water.

However, the neutralization before extracting the organic acid and organic peracid with water can not be applied on an industrial basis, from the view point of waste water treatments, which is described hereinabove.

The disadvantage in a product of 3,4-epoxycyclohexyl methyl(meth)acrylate is low in purity, for example, more specifically less than 90% in purity, and such unpurified 3,4-epoxycyclohexyl methyl (meth)acrylate undesirably has the tendency of readily polymerizing.

It is noted that there is required that the purity of the commercially available 3,4-epoxycyclohexyl methyl (meth)acrylate is from 94 to 97% by weight, and the residual components are primarily a starting material, a starting solvent and water.

From the above-described viewpoints, and as a result of studies by the present inventors, it has been found that a purified 3,4-epoxycyclohexyl methyl(meth)acrylate can be prepared by the various improved steps on a commercial basis.

SUMMARY OF THE INVENTION

An object of the present invention is to provide a purified 3,4-epoxycyclohexyl methyl (meth)acrylate and the improved processes for the preparation thereof.

A first aspect of the present invention is an improved process for the preparation of a purified 3,4-epoxycyclohexyl methyl (meth)acrylate, characterized in that a centrifugal extractor is used and retention time therethrough is adjusted within 5 minutes in extracting with water to remove the organic peracid and an organic acid derived from the organic peracid used in the epoxidation reaction.

A second aspect of the present invention is an improved process for the preparation of a purified 3,4-epoxycyclohexyl methyl (meth)acrylate, characterized in that an organic acid and organic peracid remained after extracting with water are neutralized with an aqueous alkali solution, and then separated.

A third aspect of the present invention is an improved process for the preparation of a purified 3,4-epoxycyclohexyl methyl (meth)acrylate, characterized in that 3,4-epoxycyclohexyl methyl (meth)acrylate including low-boiling ingredients is evaporated by different two stages evaporation conditions.

A fourth aspect of the present invention is a process for the preparation of a purified 3,4-epoxycyclohexyl methyl (meth)acrylate, characterized in that a crude reaction solution having 3,4-epoxycyclohexyl methyl (meth)acrylate is processed by the step:

(a) extracting said organic peracid and an organic acid in the crude reaction solution derived from said organic peracid with water using a centrifugal extractor in which retention time therethrough is adjusted within 5 minutes in extracting with water to remove the organic peracid and an organic acid derived from the organic peracid, (b) said organic solution layer being neutralized with an aqueous alkali solution to form an organic solution layer and an aqueous solution layer, said organic solution layer being separated from said aqueous solution layer, and successively (c) said organic solution layer being evaporated at temperatures not more than 100° C. and at reduced pressures to obtain a 3,4-epoxycyclohexenyl methyl (meth)acrylate solution including low-boiling ingredients of from 3 to 50% by weight, and further (d) said 3,4-epoxycyclohexenyl methyl (meth)acrylate solution being evaporated at temperatures not more-than 100° C. and at less than ½ of the reduced pressures in the above-mentioned (c) to obtain a purified 3,4-epoxycyclohexenyl methyl (meth)acrylate including the low-boiling ingredients of not more than 1% by weight.

A fifth aspect of the present invention is a 3,4-epoxycyclohexyl methyl (meth)acrylate composition including an organic phosphorous compound represented by general formulae (I) and/or (II) described hereinafter;

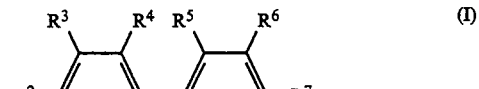

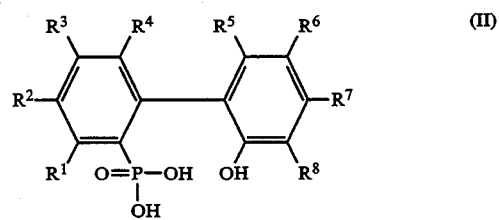

A sixth aspect of the present invention is a 3,4-epoxycyclohexyl methyl (meth)acrylate having a heptane test value of not more than 0.1%.

DETAILED DESCRIPTION OF THE INVENTION

The present invention is described hereinafter in more detail.

According to a first aspect of the present invention, there is provided an improved process for the preparation of 3,4-epoxycyclohexyl methyl (meth)acrylate by the epoxidation reaction of cyclohexenyl methyl (meth)acrylate with an organic peracid, characterized in that a centrifugal extractor is used and retention time therethrough is adjusted within minutes in extracting with water to remove the organic peracid and an organic acid derived from the organic peracid used in the epoxidation reaction.

The crude reaction solution to be used in the first aspect is prepared by the epoxidation reaction of cyclohexenyl methyl (meth)acrylate which is a main starting material, with an organic peracid.

The organic peracid includes performic acid, peracetic acid, perpropionic acid, m-chloroperbenzoic acid, trifuluoroperacetic acid and perbenzoic acid.

Of these organic peracid, peracetic acid is the preferred organic peracid, because it is available on an industrial basis at a moderate price and has a high stability.

Although the molar ratio of the organic peracid to cyclohexenyl methyl(meth)acrylate, more specifically to the double bond, is theoretically 1/1, the preferred range is from 0.1/1 to 10/1, more preferably from 0.8/1 to 1.5/1.

If the ratio is more than 10/1, although it is preferred from the view points of the conversion of cyclohexenyl methyl (meth)acrylate to epoxycyclohexyl methyl (meth)acrylate, a reduction of the time of period for epoxidizing and a reduction of product losses because of polymerization, resulting in disadvantages of a side reaction by the excess of the organic peracid or a reduction of selectivity of the organic peracid, and a considerable increase of the recovery cost of the peracid.

On the other hand, if the ratio is not more than 0.1/1, although it is preferred from the view points of a reduction of product losses, a reduction of the side reaction by the organic peracid and an increase of selectivity and further conversion of the organic peracid, resulting in a considerable increase of the recovery cost of cyclohexenyl methyl(meth)acrylate.

Accordingly, most preferably, a slightly excess amount of the organic peracid than the theoretical ratio is used because of a decomposition of the organic peracid, even though being small amounts, on the epoxidation reaction.

The epoxidation reaction can be preferably carried out in the presence of a solvent. The use of the solvent for dilution is effective for lowering the viscosity of the crude reaction solution and stabilizing the organic peracid, and further lowering the reaction velocity of resulting epoxy group with a resulting organic acid.

The preferred solvent includes an aromatic hydrocarbon, such as benzene, toluene, xylene, ethylbenzene, iso-propylbenzene, diethylbenzene, and p-simene, an aliphatic hydrocarbon such as cyclohexane, n-hexane, heptane, hexane, octane, nonane, decane and decaline, an alcohol such as cyclohexanol, hexanol, heptanol, octanol, nonanol and furfuryl alcohol, a ketone such as acetone, methyl ethyl ketone and cyclohexanone, an ester compound such as ethyl acetate, n-amylacetate, cyclohexyl acetate, isoamyl propionate, and methyl benzoate, a polyvalent alcohol such as ethylene glycol, propylene glycol, ethylene glycol monomethylether, ethylene glycol monoethylether, ethylene glycol monoethylether acetate, ethylene glycol monomethylether acetate, diethylene glycol monomethylether, diethylene glycol monoethylether an a derivative thereof, a halogenated compound such as chloroform, dimethyl chloride, carbon tetrachloride, chlorobenzene, and an ether compound such as 1,2-dimethoxyetane, etc.

For example, in case that peracetic acid is used as an organic peracid, ethyl acetate is preferably used as the solvent for dilution.

Although the molar ratio of the solvent to cyclohexenyl methyl(meth) acrylate is preferably from 0.5/1 to 5/1, more preferably from 1.5/1 to 3/1. If the ratio is less than 0.5/1, there becomes smaller the stabilizing effect to the organic peracid.

On the other hand, even though the ratio is more than 5/1, the stabilizing effect does not increase so much in comparison with an increase of costs for the recovery of the solvent.

Furthermore, a polymerization inhibitor can be used together with a gas including molecular state oxygen in the case of carrying out the epoxidation reaction.

The preferred polymerization inhibitor includes hydroquinone, hydroquinone monomethylether, p-benzoquinone, cresol, t-butylcatecol, 2,4-dimethyl-6-t-butylphenol, 2-t-butyl-4-methoxyphenol,3-t-butyl-4-methoxyphenol, 2,6-di-t-butyl-p-cresol, 2,5-dihydroxy-p-quinone, piperidine, ethanolamine, alpha-nitroso-beta-naphthol, diphenylamine, phenothiazine, N-nitrosophenylhydroxylamine and N,N-diethylhydroxylamine, etc.

The use amount of the polymerization inhibitor is preferably from 0.005 to 5%, more preferably from 0.001 to 0.1% by weight based on cyclohexenyl methyl (meth)acrylate which is a primary starting material.

Still further, a stabilizer for an organic peracid can be optionally used. The preferred stabilizer includes ammonium hydrogen phosphate, potassium pyrophosphate, sodium phosphate, potassium 2-ethylhexyl pyrophosphate, sodium 2-ethylhexyl pyrophosphate, tripolyphosphoric acid, potassium tripolyphosphate, sodium tripolyphosphate, sodium 2-ethylhexyl pyrophosphate, potassium 2-ethylhexyl pyrophosphate, tetrapolyphosphoric acid, potassium tetrapolyphosphate, sodium tetrapolyphosphate, 2-ethylhexyl tetrapolyphosphate, potassium 2-ethylhexyl tetrapolyphosphate, sodium 2-ethylhexyl tetrapolyphosphate, potassium hexametaphosphate and sodium hexametaphosphate, etc.

There can be used one or more than one stabilizer.

The use amount of the stabilizer for the organic peracid is preferably from 0.001 to 1%, more preferably from 0.01 to 0.2% by weight based on cyclohexenyl methyl (meth)acrylate which is a primary starting material, in the form of either a powder or a solution with a solvent.

The temperature region of the epoxidation reaction can be usually selected according to the reactivity of the organic peracid, that is, such that the epoxidation reaction advantageously occurs over the decomposition of the organic peracid, and further such that there does not occur the side reaction such as the opening reaction of resulting epoxy group with an organic acid derived from the organic peracid.

In the case of peracetic acid, which is the preferred organic peracid, the preferred temperature region is specifically from 0° to 70° C.

If the temperature is lower than 0° C, there requires a long time of period to complete the epoxidation reaction.

On the other hand, if the temperature is higher than 70° C., there occurs decomposition of peracetic acid.

The epoxidation reaction is usually carried out at ordinary pressure conditions, and also can be optionally carried out at reduced or pressurized conditions.

And, the epoxidation reaction is carried out by a continuous process or a batchwise process.

In the case of the continuous process, there can be preferably used a piston-flow type one, in the case of the batchwise process, there can be preferably used a semi-batch type one in which the organic peracid is successively supplied.

More specifically, the starting material and the solvent are firstly supplied into a reaction vessel, and then the catalyst and the stabilizer are optionally dissolved, and then the organic peracid is successively supplied by dropwise addition as mentioned above.

The completion of the epoxidation reaction is preferably watched by the concentration of the residual organic peracid or gas chromatography analysis. After the completion of the epoxidation reaction, extraction of the organic acid and organic peracid from the crude reaction solution with water is carried out as described below.

The crude reaction solution generally has a composition composed of 3,4-epoxycyclohexyl methyl (meth)acrylate which is a primary product, small amounts of unreacted cyclohexeyl methyl (meth)acrylate which is a starting material, the residual organic peracid which is used in slightly excess amounts, the organic acid derived from the reacted organic peracid, an optionally used polymerization inhibitor or a catalyst, and a solvent.

The crude reaction solution is supplied, as it were, as a starting material in the first aspect of the present invention.

A centrifugal extractor is essentially used in the first aspect of the present invention.

The retention time of period while passing through the extractor which corresponds to a contacting time of period between an aqueous solution and an organic solution, must be adjusted in a scope within 5 minutes, preferably within 3 minutes depending upon an approvable loss amount of 3,4-epoxycyclohexyl methyl (meth-)acrylate which is a primary product and the reaction velocity between the epoxy group and the kind of the organic acid derived from the organic peracid to be used.

The inherent minimum retention time of period depends upon a size of the centrifugal extractor to be used.

Specifically describing, a larger sized centrifugal extractor inevitably has a longer inherent minimum retention time of period.

The centrifugal extractor in which two liquids are capable of counter-currently contacting, has a rotary body or a drum integrally mounted on a rotary shaft, the rotary body or drum having a plurality of, specifically, 50 or so stages of ring members or perforated cylinders, etc.

There is assembled each stage with mixing chambers and settling chambers in the rotary body or the drum of the centrifugal extractor.

A solution to be processed initially containing a solute, and a reagent for extracting circulate counter-currently each other in the rotary body or drum, and mixing and separating operations performed in each stage allow the solute to pass into water.

In the mixing chamber, the two phases are mixed by the high relative speed between the stationary part and rotating wall.

And, in the settling chamber, the two phases previously mixed are separated by centrifugal force.

More specifically, the crude reaction solution and water which is a reagent for extracting are supplied into the rotary body or drum rotating at high speed passing through two pipes connected to a rotating shaft, respectively, and then the solution and water are contacted at the state of a counter-current.

As the result, a heavy solution phase is radially transferred to an outerward direction of the rotary body or drum by the centrifugal force, and a light solution phase is radially transferred to an innerward direction of the shaft.

There can be attained the effective extraction of the organic acid and the organic peracid from the crude reaction solution by the counter-currents and transferences at slits between the ring members or holes on perforated cylinders. The organic acid and organic peracid can be extracted with water within a short retention time passing through the extractor.

Extraction can be carried out within 5 minutes even in the case of two solutions having a small difference between specific gravities because of using the centrifugal force.

Although the time of period required to extract in the centrifugal extractor also depends upon the plate efficiency, the numbers of actual plate and the kinds of liquids, that is the specific gravity differences between two liquids, it is generally from several seconds to approximately 50 minutes or so.

Accordingly, in the case of the present invention, the epoxy group does not react with the organic peracid, the organic acid and water so much, resulting in only minor amounts of product losses.

It is noted that the mechanism and internal structures of such centrifugal type counter-current apparatus are disclosed in U.S. Pat. Nos. 3,327,939, 3,814,307, 4,225,079, 4,272,011, 4,326,666 and 4,367,202, etc.

On the other hand, apparatuses such as a mixer-settler type extractor a ring and plate type extractor and or a column type extractor, which are generally also used in extraction processes with water, can not be used for the present process because of large amounts of product losses by requiring a relatively long retention time of period, for example, from several minutes to approximately 50 minutes or so.

A reasonable separation of two liquids having the small specific gravity differences is not attainable by short retention time of period in such apparatuses.

Furthermore, small amounts of an alkali can be optionally used together with water supplied in the form of counter-current for the purpose of further effectively or completely removing the organic acid and organic peracid in the crude reaction solution.

For example, in the case of using a solvent such as ethyl acetate smaller than water in the specific gravity, the aqueous alkali solution is inevitably mixed at the zones where the concentrations of the organic acid and organic peracid become lower, more specifically at the slits or the holes in the ring members or the perforated cylinders situated near the shaft.

It is noted that the concentrations difference of the organic acid and organic peracid between in the crude reaction solution and in aqueous solution act as a driving force for the transference of them into the aqueous solution.

Accordingly, there is preferably selected the use amounts of the alkali corresponding to approximately 1% of the organic acid and organic peracid in the reaction solution, because of only supplementarily supplying into the zones mentioned above.

Furthermore, it is noted that in the case of having relatively low theoretical plate numbers, the reaction solution can also be passed through repeatedly the centrifugal extractor to be used in the present invention supplying water by counter-current.

However, if there is not required a recovery of the organic acid and organic peracid and a waste water treatment, the use amounts of the alkali are not limited.

The aqueous solution layer separated in the centrifugal extractor in which the organic acid and organic peracid extracted with water are dissolved, can not be generally discharged as a waste water without any treatments from the viewpoint of prevention of environmental pollution.

However, for example, a treatment of the solution by a neutralization with an alkali can not be applied because of a substantially same process as the neutralization before an extraction with water.

Accordingly, in the case that the boiling points of the organic acid and organic peracid are lower than the boiling points of water, they can be generally removed from the solution and they can be recovered with distillation.

On the other hand, in the case that the boiling points of the organic acid and organic peracid are higher than the boiling points of water, the organic acid and organic peracid are removed and recovered by a back extraction method from the solution using a reagent for extracting, more specifically an organic solvent.

Even in the case that the boiling points are higher than the boiling points of water, although distillation can be applied, it can not be applied on an industrial basis because of considerably large energy costs due to evaporation of water.

The preferred solvents include benzene, toluene, xylene, ethylbenzene, isopropylbenzene, diethylbenzene, p-symene, etc. which are aromatic hydrocarbons, cyclohexane, n-hexane, heptane, octane, nonane, decane, decalin, etc. which are aliphatic or alicyclic hydrocarbons, ethyl acetate, n-amyl acetate, cyclohexyl acetate, iso-amyl propionate, methyl ester of benzoic acid which are ester compounds, chloroform, carbon tetrachloride, chlorobenzene, etc. which are halogenated compounds, 1,2-dimethoxyethane, diethyl ether, etc. which are ether compounds.

There can be preferably used the solvents much lower in boiling points than the organic acid and organic peracid because of inevitably carrying out distillation after the back extraction.

Furthermore, there can be preferably used the solvents having a low solubility into water because of inevitably carrying out the waste water treatments.

The water extraction process according to the first aspect of the present invention is preferably carried out at relatively lower temperature conditions from the view point of the lower reactivity of the epoxy group in 3,4-epoxycyclohexyl methyl (meth)acrylate with the organic acid.

However, too low temperature conditions occasionally make the property for separating into the two solution layers lower because of an increase of the viscosity and a decrease of the gravity differences.

Accordingly, the preferred temperature range is from 10° to 30° C., more preferably from 15° to 25° C.

It is noted that the organic acid and also organic peracid should be removed to the extent of less than 0.1%, preferably less than 0.05%, respectively, in the reaction solution after extraction in order to sufficiently remove the organic acid and organic peracid in a next process which is an alkali neutralization process and from the view point of reducing the load of a waste water treatment.

Although there is not limited the supplying ratio of water which is a reagent for extracting the organic acid and organic peracid to the crude reaction solution in the extraction process with water, it is preferably from ½ to 3/1 by weight in order to attain the above-mentioned concentrations of the organic acid and peracid.

According to a second aspect of the present invention, there is provided an improved process for the preparation of a purified 3,4-epoxycyclohexyl methyl (meth)acrylate by the epoxidation reaction of cyclohexenyl methyl (meth)acrylate with an organic peracid, characterized in that an organic acid and an organic peracid are removed from a crude reaction solution after the epoxidation reaction by extraction with water and successively neutralized with an aqueous alkali solution.

In the second aspect of the present invention, a solution to be supplied must be the solution after extracting the organic acid and organic peracid with water, which is more specifically, the solution having the organic acid and organic peracid of less than 0.1%, more preferably less than 0.05%.

And, the organic acid and organic peracid must be removed to the extent of less than 0.01% in the alkali neutralization in order to obtain a purified 3,4-epoxycyclohexyl methyl (meth)acrylate.

Although depending upon the concentrations of the residual organic acid and organic peracid after extraction with water, the concentration of the aqueous alkali is generally from 0.1% to 10%, more preferably from 1 to 2%.

If it is more than 10%, for example, ethyl acetate which is a preferred solvent in the epoxidation reaction occasionally exhibits the tendency of a decomposition.

On the other hand, if it is less than 0.1%, the organic acid and organic peracid cannot sufficiently removed.

The preferred temperatures range is from 0° to 50° C., preferably from 10° to 30° C. In the case of less than 0° C., it is difficult to separate into two solution layers. On the other hand, in the case of more than 50° C., organic components tend to be dissolved into the aqueous alkali solution, resulting in increasing the load of a waste water treatment.

The neutralization with the aqueous alkali can be carried out by a continuous process or a batchwise process.

In the case of the continuous process, a mixer-settler type apparatus can be preferably used.

It is noted that the above-mentioned centrifugal counter-current extractor is not preferably used in the alkali neutralization process because of the short retention time of period, resulting in insufficient removal of the organic acid and peracid.

In the case of the batchwise process, an extracting column type apparatus can be preferably used.

In the alkali neutralization process, the residual (unreacted and remained in the extraction process with water) organic peracid must be sufficiently removed together with the organic acid, for example, to the extent of not more than 0.01% by weight based on the reaction solution, for the purpose of a stabilized operation of evaporation in order to remove low-boiling ingredients.

According to a third aspect of the present invention, there is provided an improved process for the preparation of a purified 3,4-epoxycyclohexylmethyl (meth)acrylate by the epoxidation reaction of cyclohexenyl-methyl (meth)acrylate with an organic peracid, characterized in that a 3,4-epoxycyclohexyl methyl (meth)acrylate solution including low-boiling ingredients is refined by the step:
  (a) evaporating components having low boiling points at temperatures not more than 100° C. and at reduced pressures to obtain a crude epoxidized solution including low-boiling ingredients of from 3 to 50% by weight
and successively
  (b) evaporating the low-boiling ingredients at temperatures not more than 100° C. and at less than ½ of the reduced pressures in above-mentioned (a) to obtain 3,4-epoxycyclohexenyl methyl (meth)acrylate including the low-boiling ingredients of not more than 1% by weight.

The solution to be supplied into a first evaporator preferably has a composition composed of 3,4-epoxycyclohexyl methyl (meth)acrylate which is a primary desired product, small amounts of unreacted cyclohexenyl methyl (meth)acrylate which is a starting material, the small amounts of the organic peracid and the organic acid unremoved in the extracting process with water and/or in the neutralization process with the aqueous alkali solution, a solvent which is a primary low-boiling ingredients to be evaporated, and further small amounts of by-products.

More specifically, the contents of the residual organic peracid and organic acid in the solution must be preferably reduced to the extent of less than 100 ppm, respectively.

If the contents are more than 100 ppm, the epoxy group in 3,4-epoxycyclohexyl methyl (meth)acrylate reacts with the organic acid under the influence of heating in evaporation, resulting in polymerization of 3,4-epoxycyclohexyl methyl (meth)acrylate and in causing suspensions in a heptane test described hereinabove, specifically, a heptane test value of approximately 0.1% or more.

Although depending upon the kinds of solvents or organic peracids to be used in the epoxidation reaction, the preferred temperatures in evaporation are less than 100° C., more specifically from 40° to 60° C., from the view point of preventing polymerization of 3,4-epoxycyclohexyl methyl (meth)acrylate.

If the temperatures are more than 100° C., there readily tends to cause the polymerization of 3,4-epoxycyclohexyl methyl (meth)acrylate and cyclohexenyl methyl(meth)acrylate, even though at small amounts of the organic peracid and organic acid.

If the temperatures are less than 40° C., it is too low in the evaporation velocity.

The evaporations are preferably carried out with a thin-film evaporator.

The reduced pressures range in the first step evaporation is from 100 to 200 Torr depending upon the kinds of solvents or organic peracids to be used in the epoxidation reaction, preferably from 100 to 150 Torr.

And, the reduced pressures range in the second step evaporation is essentially less than ½ of the first step reduced pressures, preferably from ⅓ to ¼.

The low-boiling ingredients include solvents, water and minor amounts of the organic acid and organic peracid.

The evaporation process which is the third aspect of the present invention is characterized by being separated into the two stages having different evaporation conditions, and also particularly characterized by controlling the contents of the low-boiling ingredients remained in the first stage evaporation.

The third aspect is based on the mechanism that although initial evaporation of the low-boiling ingredients is relatively easy even though under lowerly reduced pressure conditions, final evaporation is relatively difficult without highly reduced pressure conditions.

That is, the contents of the low-boiling ingredients are essentially maintained in the range of from 3 to 50% by weight based on the total weight of the crude reaction solution, preferably from 5 to 20% by weight, more preferably 10% or so.

If the contents are less than 3% by weight, there is required the highly reduced pressure in the first stage evaporation and the evaporated solvents can not be economically recovered without many losses in the case of catching by a condenser.

On the other hand, if the contents are more than 50% by weight, solvents can not be economically recovered without many losses in the case of catching by a condenser because of the highly reduced pressures in the second stage.

The contents of the low-boiling ingredients in the product under the second stage evaporation are essentially not more than 1% by weight.

If the contents are more than 1%, the product primarily including 3,4-epoxycyclohexyl methyl (meth)acrylate is not commercially available.

According to a fourth aspect of the present invention, there is provided a process for the preparation of a purified 3,4-epoxycyclohexyl methyl (meth)acrylate from a crude reaction solution obtained by the epoxidation reaction of cyclohexenyl methyl (meth)acrylate with an organic peracid, characterized by the step:
  (a) extracting said organic peracid and an organic acid in the crude reaction solution derived from said organic peracid with water using a centrifugal extractor in which retention time is adjusted within less than 5 minutes in extracting with water to remove the organic peracid and an organic acid derived from the organic peracid,
  (b) said organic solution layer being neutralized with an aqueous alkali solution to form an organic solution layer and an aqueous solution layer, said organic solution layer being separated from said aqueous solution layer,
and successively
  (c) said organic solution layer being evaporated at temperatures not more than 100° C. and at reduced pressures to obtain a 3,4-epoxycyclohexenyl methyl (meth)acrylate solution including low-boiling ingredients of from 3 to 50% by weight,
and further
  (d) said 3,4-epoxycyclohexenyl methyl (meth)acrylate solution being evaporated at temperatures not more than 100° C. and at less than ½ of the reduced pressures in the above-mentioned (c) to obtain a purified 3,4-epoxycyclohexenyl methyl (meth)acrylate including the low-boiling ingredients of not more than 1% by weight.

The fourth aspect is composed of a series of the combination of the above-mentioned first aspect, second aspect and third aspect.

According to a fifth aspect of the present invention, there is provided a 3,4-epoxycyclohexyl methyl (meth)acrylate composition including from 0.01 to 0.1 parts by weight of an organic phosphorous compound represented by general formulae (I) and/or (II) described hereinafter;

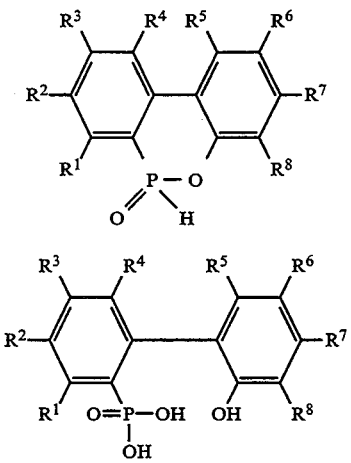

[in the formulae (I) and (II), $R^1$ to $R^8$ are hydrogen, a halogen, and or a monovalent aliphatic or aromatic substituent group having carbon numbers of from 1 to 10, which may be same or different, respectively]. The organic phosphorous compounds are used for the purpose of preventing coloring of 3,4-epoxycyclohexyl methyl (meth)acrylate, in the present invention.

As described previously, it is known that 3,4-epoxycyclohexyl methyl (meth)acrylate is exceedingly readily colored in the preparation processes, while being stored and/or shipped because of oxidation by air or other causes. For example, it appears as a mechanism of coloring that 3,4-epoxycyclohexyl methyl (meth)acrylate itself polymerizes or by-reacts, even though in very minor amounts, because of its high reactivity.

The preferred color hue value in a commercially available 3,4-epoxycyclohexyl methyl (meth)acrylate is usually less than 200 in APHA value, if taking it into consideration of the various uses, desirably less than 100.

It may be generally considered that purification of 3,4-epoxycyclohexyl methyl (meth)acrylate by distillation is suitable for a method for preventing coloring.

However, it is not preferable due to history of heating even though under reduced pressures.

Accordingly, it appears that a chemical treatment or an absorption treatment is more preferable instead of distillation.

In the chemical treatment, for example, there have been added molecular state oxygen, an oxidant such as hydrogen peroxide, a reducing agent such as sodium borohydride, sodium hydrogenated bis(2-methoxyethoxy)aluminum, a polymerization inhibitor such as hydroquinone, an antioxidant such as BHT (2,6-ditert-butyl-4-methyl-phenol), BHA (butyl hydroxy anisole), a blocking agent for metal such as EDTA, trioctyl phthalate, etc. in the preparation processes.

In the absorption treatment, for example, it is known that there have been used an activated carbon which is a most conventional absorbent, an activated clay, zeolite, a highly porous polymer, etc.

However, there are only very minor effects for preventing coloring or for discoloring according to such conventional chemical treatment or absorption treatment.

Furthermore, Japanese Patent Application No. 191267/1990 discloses the use of a hydrotalcite compound for removing coloring components in 3,4-epoxycyclohexyl methyl (meth)acrylate.

However, there causes coloring again after a long time of period in the use of the compound.

The essential organic phosphorous compound include 3,4,5,6-dibenzo-1,2-oxaphosphane-2-oxide, 9,10-dihydro-9-oxa-10-phosphaphenanthrene-10-oxide (for example, HCA which is a trade name, manufactured by Sanko Chemical, Ltd.), 6,8-dichloro-9,10-dihydro-9-oxa-10-phosphaphenanthrene-10-oxide, 6,8-di(tert-butyl)-9,10-dihydro-9-oxa-10-phosphaphenanthrene-10-oxide, etc., and further a hydrated compound thereof.

The organic phosphorous compounds are represented By formula

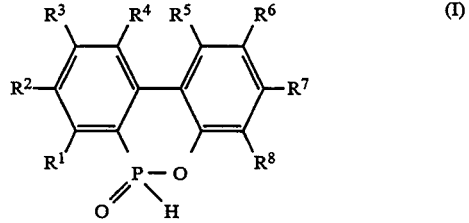

and the hydrated compound are represented by formula (II);

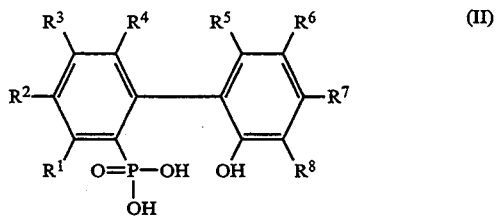

[in the formulae (I) and (II), $R^1$ to $R^8$ are hydrogen, a halogen, and or a monovalent aliphatic or aromatic substituent group having carbon numbers of from 1 to 10, which may be same or different, respectively].

The organic phosphorous compounds can be added either in the form of powder or a solution with a solvent.

Although the organic phosphorous compounds may also be added even in the each step of the present preparation process, it is preferably mixed in a final product.

The use amounts of the compound represented by formulae (I) and (II) are essentially from 0.001 to 1 part, preferably from 0.01 to 0.2 part by weight.

If the use amounts are less than 0.001 parts by weight, the effect as a polymerization inhibitor is small.

On the other hand, if the use amounts are more than 1 part by weight, there causes an adverse affection instead of the effect as a polymerization inhibitor.

According to a sixth aspect of the present invention, there is provided 3,4-epoxycyclohexyl methyl (meth)acrylate having a heptane test value of less than 0.1% by weight.

The 3,4-epoxycyclohexyl methyl (meth)acrylate having a heptane test value of less than 0.1% by weight can be prepared by the combined processes of the above-mentioned first aspect, second aspect and third aspect, and or fourth aspect alone.

The heptane test value relating to a conventional 3,4-epoxycyclohexyl methyl (meth)acrylate has been more than 0.1% by weight, more specifically approximately 0.14% by weight or so.

The heptane test value corresponds to the amounts of polymers having a low molecular weight composed of 3,4-epoxycyclohexyl methyl (meth)acrylate itself.

The contents of the polymers having a low molecular weight can be shown by weight % with a measuring method using n-heptane or n-hexane, in which 10 g of a product is dissolved in 100 cc of n-heptane or n-hexane and resulting suspensions are filtered and weighed.

3,4-epoxycyclohexyl methyl (meth)acrylate prepared by the combined processes of the above-mentioned first aspect, second aspect and third aspect, and or fourth aspect alone exhibits usually the heptane test value of 0.02% by weight or so.

In the following, Synthesis Examples, Examples and Comparative Examples are described in order to more specifically illustrate the present invention.

SYNTHESIS EXAMPLE 1

Preparation of a Crude Reaction Solution Including 3,4-Epoxycyclohexyl Methyl Methacrylate A SUS 816-made reaction vessel having a capacity of 15 liter equipped with a stirrer and a jacket for cooling was charged with 3913 parts of 3-cyclohexenyl methyl (meth)acrylate (hereinafter, referred to as CHMA), 7826 parts of ethyl acetate, 5.85 parts of hydroquinone monomethylether which is a polymerization inhibitor and 2.35 parts of sodium tripolyphosphate which is a stabilizer for a peracid, followed by raising the internal temperature to 45° C.

Successively, 6329 parts of ethyl acetate solution including 30% of peracetic acid was added dropwise over 4 hours, followed by aging for 2 hours. The internal temperature was maintained at 50° C. while adding dropwise and aging, to obtain 18076 parts of a crude reaction solution including 3,4-epoxycyclohexyl methyl methacrylate (hereinafter, referred to as METHB).

Example 1—A Water Extraction Test with a Centrifugal Extractor

The crude reaction solution obtained in Synthesis Example 1 was introduced from an inlet for a light solution phase at 2108 g/minute and water was introduced from an inlet for a heavy solution phase at 3590 g/minute into a counter-current type centrifugal extractor (having priming volume of 2400 ml) equipped with a rotor having an outer diameter of 46 cm and an inner diameter of 25 mm which rotates at 4000 r.p.m.

And, a light solution layer was obtained at 1664 g/minute from an outlet for the light solution layer and a heavy solution layer was obtained at 4034 g/minute from an outlet for the heavy solution layer.

Retention time of period in the centrifugal extractor was approximately 25 seconds.

The light solution layer was introduced again from the inlet for the light solution layer at 2108 g/minute and water was introduced from the inlet for the heavy solution layer at 3590 g/minute.

And, a light solution layer was obtained at 1877 g/minute from the outlet for the light solution layer and a heavy solution layer was obtained at 3821 g/minute from the outlet for the heavy solution layer.

Retention time of period in the centrifugal extractor was approximately 25 seconds.

Accordingly, the total retention time of period was approximately 50 seconds.

The concentrations of acetic acid and peracetic acid in the crude reaction solution before extracting with water were 10.66% and 1.15%, respectively.

The concentrations of acetic acid and peracetic acid in the light solution layer after extracting in twice with water were 400 ppm and 150 ppm, respectively.

99% of METHB dissolved in the crude reaction solution was recovered in the light solution layer after extracting in twice with water.

Comparative Example 1—A Water Extraction Test Supposing a Column Type Extractor A flask having a capacity of 2 liter equipped with a stirrer was charged with 1000 parts of a crude reaction solution obtained by the same procedures as described in Synthesis Example 1 and 1000 parts of water, followed by agitating for 60 minutes at 20° C. and settling for 30 minutes.

As the result, approximately 5% of METHB dissolved in the crude reaction solution disappeared under the influence of the reaction of METHB with an aqueous acetic acid solution.

Synthesis Example 2—Preparation of a Crude Reaction Solution Including 3,4-Epoxycyclohexyl Methyl Acrylate A SUS 316-made reaction vessel having a capacity of 20 liter equipped with a stirrer and a jacket for cooling was charged with 3000 parts of 3-cyclohexenyl methyl acrylate (hereinafter, referred to as CHAA), 11100 parts of ethyl acetate, 0.9 part of hydroquinone monomethylether which is a polymerization inhibitor and 9.0 parts of sodium tripolyphosphate, followed by introducing a mixed gas composed of oxygen and nitrogen (oxygen/nitrogen=10/90 by volume) at 32 normal liter/hour from a tube and raising the internal temperature to 40° C.

Successively, 5623 parts of ethyl acetate solution including 30% of peracetic acid was added dropwise over 4 hours with a pump maintaining the reaction temperature at 40° C., followed by aging for 5 hours after the addition of peracetic acid to complete the epoxidation reaction and to obtain 19723 parts of a crude reaction solution including 3,4-epoxycyclohexyl methyl acrylate (hereinafter, referred to as AETHB).

Example 2—A Water Extraction Test with a Centrifugal Extractor

The crude reaction solution obtained in Synthesis Example 2 was introduced from an inlet for a light solution phase at 2108 g/minute and water was introduced from an inlet for a heavy solution phase at 3621 g/minute into a counter-current type centrifugal extractor (having priming volume of 2400 ml) equipped with a rotor having an outer diameter of 46 cm and an inner diameter of 25 mm which rotates at 4000 r.p.m.

And, a light solution layer was obtained at 1713 g/minute from an outlet for the light solution phase and a heavy solution layer was obtained at 4016 g/minute from an outlet for the heavy solution phase.

Retention time of period in the centrifugal extractor was approximately 25 seconds.

The light solution layer was introduced again from the inlet for the light solution phase at 2108 g/minute and water was introduced from the inlet for the heavy solution phase at 3590 g/minute.

And, a light solution layer was obtained at 1865 g/minute from the outlet for the light solution phase and a heavy solution layer was obtained at 3833 g/minute from the outlet for the heavy solution phase.

Retention time of period in the centrifugal extractor was approximately 25 seconds.

Accordingly, the total retention time of period was approximately 50 seconds.

The concentrations of acetic acid and peracetic acid in the crude reaction solution before extracting with water were 8.96% and 1.51%, respectively.

The concentrations of acetic acid and peracetic acid in the light solution layer after extracting in twice with water were 400 ppm and 150 ppm, respectively.

99% of AETHB dissolved in the crude reaction solution was recovered in the light solution layer after extracting in twice with water.

Example 3—An Alkali Neutralization Test

A SUS 316-made vessel for mixing equipped with a stirrer and a jacket for cooling having a capacity of 15 liter was charged with 3000 parts of the light solution layer obtained in Example 2, successively, 3000 parts of an aqueous solution including 1% of NaOH was charged into the vessel, followed by agitating for 1 hour maintaining at the temperature of 10° C.

After settling for 30 minutes, 2790 parts of an upper solution layer was separated from a lower solution layer.

The concentrations of acetic acid and peracetic acid in the upper solution layer were less than 100 ppm, respectively.

Example 4—An Alkali Neutralization Test

The same procedures as described in Example 3 were repeated, except that there was charged 3000 parts of an aqueous solution including 0.5% of NaOH.

The concentrations of acetic acid and peracetic acid in the upper solution layer were less than 100 ppm, respectively.

Example 5—An Alkali Neutralization Test

The same procedures as described in Example 5 were repeated, except that there was charged 3000 parts of an aqueous solution including 0.1% of NaOH.

The concentrations of acetic acid and peracetic acid in the upper solution layer were less than 100 ppm, respectively.

Example 6—An Alkali Neutralization Test

The same procedures as described in Example 3 were repeated, except that there was charged 300 parts of an aqueous solution including 1% of NaOH. The concentrations of acetic acid and peracetic acid in the upper solution layer were less than 100 ppm, respectively.

Comparative Example 2—A Water Extraction Test Supposing a Column Type Extractor

A SUS316-made mixing vessel having a capacity of 15 liter equipped with a stirrer was charged with 3000 parts of a crude reaction solution obtained by the same procedures as described in Synthesis Example 2 and 3000 parts of a distilled water, followed by agitating for 60 minutes at 10° C. and settling for 60 minutes, resulting in two solution layers.

2790 parts of the light solution layer was separated from the heavy solution layer.

As the result, approximately 5% of AETHB dissolved in the crude reaction solution disappeared under the influence of the reaction of AETHB with an aqueous acetic acid.

Comparative Example 3—An Evaporation Test After a Water Extraction Test Supposing a Column Type Extractor and without Neutralization with an Aqueous Alkali Solution 0.21 part of hydroquinone monomethylether was added in 2790 parts of the upper solution layer obtained in Comparative Example 2, the solution was supplied into a SUS-made Smith falling film type evaporator maintained at the temperature of 60° C. and the reduced pressure of 150 mm Hg supplying a mixed gas composed of oxygen and nitrogen at 32 liter/hour from the bottom of the evaporator, to which a line for discharging a liquid is connected, to obtain a solution including 5% of low boiling components.

Successively, the solution discharged from the bottom was supplied again into the SUS-made Smith falling film type evaporator at the temperature of 60° C. and the reduced pressure of 40 mm Hg supplying a mixed gas composed of oxygen and nitrogen at 32 liter/hour from the bottom of the evaporator to which a line for discharging a liquid is connected, to obtain 538 parts of a product including not more than 1% of low boiling ingredients.

The concentration of AETHB in the product was 86.5% by a gas chromatography analysis.

Example 7—An Evaporation Test 0.21 part of hydroquinone monomethylether was added in 2790 parts of the upper solution layer obtained in Example 3, the solution was supplied into a SUS-made Smith falling film type evaporator maintained at the temperature of 60° C. and the reduced pressure of 150 mm Hg supplying a mixed gas composed of oxygen and nitrogen at 32 liter/hour from the bottom of the evaporator, to which a line for discharging a liquid is connected, to obtain a solution including 5% of low-boiling ingredients.

Successively, the solution discharged from the bottom was supplied again into the SUS-made Smith falling film type evaporator at the temperature of 60° C. and the reduced pressure of 40 mm Hg supplying a mixed gas composed of oxygen and nitrogen at 32 liter/hour from the bottom of the evaporator to which a line for discharging a liquid is connected, to obtain 538 parts of a product including not more than 1% of low-boiling ingredients.

The concentration of AETHB in the product was 96.4% by a gas chromatography analysis.

The heptane test value of the product was 0.02%.

Example 8—An Evaporation Test

The same procedures as described in Example 7 were repeated, except that the upper solution layer obtained in Example 4 was used to obtain 538 parts of a product. The concentration of AETHB in the product was 95.7% by a gas chromatography analysis.

The heptane test value of the product was 0.02%.

Comparative Example 4—An Evaporation Test without Neutralization with Alkali after Extracting with Water 0.21 part of hydroquinone monomethylether was added in 2300 parts of the same upper solution layer as obtained in Example 1, the solution was supplied into a SUS-made Smith falling film type evaporator maintained at the temperature of 60° C. and the reduced pressure of 150 mm Hg supplying a mixed gas composed of oxygen and nitrogen at 32 liter/hour from the bottom of the evaporator, to which a line for discharging a liquid is connected, to obtain a solution including 5% of low-boiling ingredients.

Successively, the solution discharged from the bottom was supplied again into the SUS-made Smith falling film type evaporator at the temperature of 60° C. and the reduced pressure of 40 mm Hg supplying a mixed gas composed of oxygen and nitrogen at 32 liter/hour from the bottom of the evaporator to which a line for discharging a liquid is connected, to obtain a product including not more than 1% of low-boiling ingredients.

The concentration of METHB in the product was 89.5% by a gas chromatography analysis.

Example 9—A Coloring Test after Mixing an Organic Phosphorous Compound 0.1 part of 9,10-dihydro-9-oxa-10-phosphaphenanthrene-10-oxide was mixed with 100 parts of the product which has a color hue of 40 in APHA value obtained in Example 7.

The mixture was stored for three months at 30° C. As the result, the APHA value changed to 50.

Comparative Example 4—A Coloring Test without Mixing an Organic Phosphorous Compound The product which has a color hue of 40 in APHA value obtained in Example 7 without mixing any additives was stored for three months at 30° C. As the result, the APHA value changed to 400.

Comparative Example 5—A Coloring Test after Mixing Large Amounts of an Organic Phosphorous Compound 1 part of 9,10-dihydro-9-oxa-10-phosphaphenanthrene-10-oxide was mixed with 100 parts of the product which has AETHB contents of 96.4 obtained in Example 7. The mixture was stored for three months at 30° As the result, the AETHB contents changed to 91.2%.

Comparative Example 6—A Coloring Test after Mixing Small Amounts of an Organic Phosphorous Compound 0.001 part of 9,10-dihydro-9-oxa-10-phosphaphenanthrene-10-oxide gas mixed with 100 parts of the product which has a color hue of 40 in APHA value obtained in Example 7. The mixture was stored for three months at 30° C. As the result, the APHA value changed to 130.

Comparative Example 7—A Coloring Test after Mixing of a Conventional Coloring Inhibitor 0.1 part of BHT which is an antioxidant was mixed with 100 parts of the product which has a color hue of 40 in APHA value obtained in Example 7. The mixture was stored for three months at 30° C. As the result, the APHA value changed to 150.

Comparative Example 8—A Coloring Test after Mixing of a Conventional Coloring Inhibitor 0.1 part of BHA which is an antioxidant was mixed with 100 parts of the product which has a color hue of 40 in APHA value obtained in Example 7. The mixture was stored for three months at 30° C. As the result, the APHA value changed to 180.

Comparative Example 9—A Coloring Test after Mixing of a Conventional Coloring Inhibitor 0.1 part of Irganox (manufactured by Ciba-Geigy Corp.) which is an antioxidant was mixed with 100 parts of the product which has a color hue of 40 in APHA value obtained in Example 7.

The mixture was stored for three months at 30° C. As the result, the APHA value changed to 160.

Comparative Example 10—A Coloring Test after Mixing of a Conventional Coloring Inhibitor 0.1 part of Sanol (manufactured by Ciba-Geigy Corp.) which is an antioxidant was mixed with 100 parts of the product which has a color hue of 40 in APHA value obtained in Example 7.

The mixture was stored for three months at 30° C. As the result, the APHA value changed to 350.

Comparative Example 11—An Evaporation Test after Alkali Neutralization Treatments Thrice without Extraction with Water 3000 parts of a crude reaction solution obtained by the same procedures as described in Synthesis Example 2 was mixed with 2500 parts of an aqueous solution including 10% of NaOH, followed by stirring for 30 minutes and settling for 30 minutes, and then followed by separating the reaction solution.

The separated solution was mixed again with 2500 parts of an aqueous solution including 10% of NaOH, followed by stirring for 30 minutes and settling for 30 minutes, and then followed by separating the reaction solution.

The contents of peracetic acid in the separated solution were 0.02%, and acetic acid was completely removed.

The separated solution was further mixed with 2500 parts of an aqueous solution including 1% of NaOH, followed by stirring for 30 minutes and settling for 30 minutes, and then followed by separating the reaction solution. The contents of peracetic acid in the separated solution were less than 100 ppm.

The same procedures as described in Example 7 were repeated, except that the solution obtained in the alkali neutralization treatments was used to obtain a product.

The concentration of AETHB in the product was 94.5% by a gas chromatography analysis. And, the contents of ethyl acetate, CHAA and other components were 1.8%, 1.0% and 2.7%, respectively.

The heptane test value of the product was 0.25%, despite of evaporation in peracetic acid contents of less than 100 ppm and complete removal of acetic acid, because of a long contacting time under the coexistence of peracetic acid, acetic acid and water.

Examples 10 to 12—Water Extraction Tests with a Centrifugal Extractor

Same procedures as described in Example 1 were repeated, except that the reaction crude solution containing 3,4-epoxycyclohexyl methylmethacrlate(METHB) obtained in Synthesis Example 1 was charged into the centrifugal extractor while adjusting charging speeds[corresponding to the respective retention time of period (R.T)] as shown in Table 1.

TABLE 1

| | A1 | B1 | A2 | B2 | R.T. | R.R. |
|---|---|---|---|---|---|---|
| Example 10 | 586 | 997 | 583 | 994 | 91 | 99 |

TABLE 1-continued

| | A1 | B1 | A2 | B2 | R.T. | R.R. |
|---|---|---|---|---|---|---|
| Example 11 | 351 | 615 | 348 | 611 | 299 | 97 |
| Example 12 | 176 | 305 | 178 | 310 | 594 | 96 |

A1: Charging speed (g/minute) of reaction crude solution in first extraction
B1: Charging speed (g/minute) of water in first extraction
A2: Charging speed (g/minute) of reaction crude solution in second extraction
B2: Charging speed (g/minute) of water in second extraction
R.T.: Retention time of period (second)
R.R.: Recovery ratio (%) of METHB
99%, 97% and 96% of METHB dissolved in the crude reaction solution were recovered in the light solution layer after extracting in twice with water, respectively.

While the invention has been described in detail and with reference to specific embodiments thereof, it will be apparent to one skilled in the art that various changes and modifications can be made therein without departing from the spirit and scope thereof.

What is claimed is:

1. A 3,4-epoxycyclohexenyl methyl (meth)acrylate composition including from 0.01 to 0.1 part by weight of an organic phosphorous compound represented by general formulae (I) and/or (II):

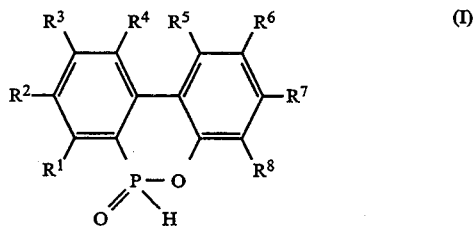

(I)

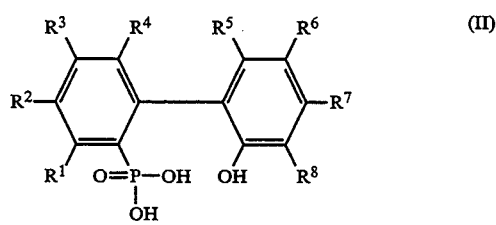

(II)

* * * * *

UNITED STATES PATENT AND TRADEMARK OFFICE
CERTIFICATE OF CORRECTION

PATENT NO. : 5,426,193
DATED : June 20, 1995
INVENTOR(S) : KUWANA et al.

It is certified that error appears in the above-indentified patent and that said Letters Patent is hereby corrected as shown below:

Col. 7, line 21, after "(meth)acrylate to" insert -- 3,4- --.
Col. 13, line 58, delete "Tort" and insert -- Torr --.
Col. 17, line 23, delete "816" and insert -- 316 --.

<u>In the Claims:</u>   Column 24, line 1-20

Claim 1, after the formula, insert

-- [in the formula (I) and (II), $R^1$ to $R^8$ are hydrogen, a halogen, and or a monovalent aliphatic or aromatic substituent group having carbon numbers of from 1 to 10, which may be same or different, respectively]. --

Signed and Sealed this

Twenty-sixth Day of September, 1995

Attest:

BRUCE LEHMAN

*Attesting Officer*          *Commissioner of Patents and Trademarks*